United States Patent [19]

Peyman

[11] Patent Number: 4,685,922
[45] Date of Patent: Aug. 11, 1987

[54] ALTERABLE REFRACTIVE POWER INTRAOCULAR LENSES

[76] Inventor: Gholam A. Peyman, 535 N. Michigan Ave., Apt. 3001, Chicago, Ill. 60611

[21] Appl. No.: 878,368
[22] Filed: Jun. 25, 1986
[51] Int. Cl.⁴ ............................................. A61F 2/16
[52] U.S. Cl. ....................................................... 623/6
[58] Field of Search ............................................ 623/6

[56] References Cited

U.S. PATENT DOCUMENTS

| | | | |
|---|---|---|---|
| 4,253,199 | 3/1981 | Banko | 623/6 |
| 4,373,218 | 2/1983 | Schachar | 623/6 |
| 4,573,998 | 3/1986 | Mazzocco | 623/6 |
| 4,585,457 | 4/1986 | Kalb | 623/6 |

Primary Examiner—Ronald L. Frinks
Attorney, Agent, or Firm—Thomas A. Kmiotek

[57] ABSTRACT

Disclosed are intraocular lenses where the refractive power is fixed at implantation while offering the benefit of changing the refractive power subsequently with little or no surgical invasion and in a nearly atraumatic manner. The intraocular lenses are comprised of a central lenticular portion having a chamber therein and having at least one refractive, rupturable membrane which can be ruptured subsequent to implantation thus changing the refractive power of the lenses. The intraocular lenses can be implanted in either the posterior chamber or capsular bag.

14 Claims, 7 Drawing Figures

ALTERABLE REFRACTIVE POWER INTRAOCULAR LENSES

FIELD OF THE INVENTION

Intraocular lenses for implanting inside aphakic eyes are the general province of this invention. This invention specifically relates to intraocular lenses whose central lenticular means has at least one chamber means therein. The chamber means either can be evacuated or can contain a material having a refractive power different from that comprising the central lenticular means, preferably a physiologically compatible material such as silicones, gelatins, polyvinyl alcohols or the like. Lenses having one chamber means therein utilize an exterior face of the central lenticular means as a refractive, rupturable membrane means. Lenses having at least two chamber means therein can use the exterior faces of the central lenticular means as refractive rupturable membrane means, can have the chamber means separated by a refractive rupturable membrane means, or can use both the exterior faces of the central lenticular means as refractive rupturable membrane means and have the chamber means separated by refractive, rupturable membrane means. This design obviates the need to remove an implanted lens that no longer is the correct refractive power. Rupturing an exterior face functioning as a refractive membrane means or the refractive membrane means separating the chamber means eliminates a refractive surface, thus changing the refractive power of the implanted lens. Rupturing an exterior face functioning as a refractive membrane means or the refractive membrane means separating the chamber means is accomplished using currently available, non-invasive techniques, such as laser radiation.

The intraocular lenses of this invention can be implanted either in the posterior chamber or in the capsular bag. After placement in the eye, if it becomes necessary to change the lens' refractive power, non-invasive techniques can accomplish the change. Typically treatment can be conducted on an "out-patient" basis.

BACKGROUND OF THE INVENTION

Currently, cataract extraction is the most common ophthalmic surgical procedure performed in the United States. Roughly, over 450,000 lenses are removed every year. These natural lenses, however, must be replaced with a prosthetic optical device before useful vision can be restored to the operated eye. Light rays no longer are focused on the retina with the lens removed. Vision is very poor without corrective glasses, contact lenses or an intraocular lens.

Corrective eye glasses have been the classic and most common method of correcting aphakia. Unfortunately, corrective glasses, being located in front of the normal position of the human lens, can produce magnification which distorts the shape of viewed objects. Contact lenses cause less magnification and distortion, but very old and very young patients frequently find handling and wearing these small lenses difficult.

There is little or no magnification or distortion with implanted intraocular lenses. Also, there is no need to remove the intraocular lens from the eye or otherwise handle the lens. Generally, intraocular lenses provide good visual acuity at all times, even at night.

Intraocular lenses have definite advantages in terms of vision and convenience over the other methods of aphakic correction. While intraocular lenses have definite advantages over corrective glasses and contact lenses, intraocular lenses have specific disadvantages.

Intraocular lens implantation surgery is more traumatic than simple cataract extraction alone. Additional handling of the cornea and manipulation inside the anterior chamber during lens implantation add to the amount of trauma to the eye. Extreme care must be exercised to limit trauma to the cornea, structures of the anterior chamber, and other structures.

Generally, during implant surgery, a 7-8 mm incision is made in the conjunctiva just outside the cornea so that the patient's natural lens can be removed and replaced with an implant intraocular lens. Incision length is dictated more by the size of the intraocular lens to be implanted than by the requirement of removing the patient's natural lens. For example, the patient's natural lens can be removed using an ultrasonic instrument which requires an incision much smaller than is needed to insert intraocular lens implants currently available.

The ability to change refractive power of an implanted intraocular lens without an additional surgical implant operation would be a desired benefit. It is particularly desirable in very young patients. Size and shape of the eyeball in very young patients change as they mature. The distance from the lens to the retina changes as the size of the eye changes. A lens of the correct refractive power when implanted may not later correctly focus light entering the eye and passing to the retina. Changes in the refractive power of lenses in very young patients may be indicated after as little time as one year. It is the antithesis of limiting trauma associated with lens implants when a surgical procedure is dictated within such a short period of time.

A large number of different types and styles of intraocular lenses has been developed. Major classes of lenses can be distinguished based on the method of fixation in the eye. Anterior chamber lenses lie entirely in front of the iris. Iris-supported lenses rely on the structural integrity of the iris to stabilize and support the lens within the eye. Capsule-fixated lenses are inserted into a planned extracapsular cataract extraction space between the iris and posterior leaves of the lens capsule. Common to most lenses in use today are their reliance on haptics, also called feet or loops, emanating from the lenses and intended to support and fix the lens in the eye.

A major concern of ophthalmic surgeons is choosing the correct refractive power for lenses. Patients risk additional surgery for lens removal and replacement if the choice of lens refractive power is or subsequently becomes too much in error. Despite diligence in choosing a lens with the correct refractive power at the time of implant, subsequent ophthalmic changes may dictate the removal of an existing implanted lens and replacement with another prosthetic lens of different refractive power. A risk commonly shared in the use of solid, silicone, and gel-type intraocular lenses is additional surgery since it is the only alternative for changing a refractive power too much in error.

A substantive effort to avoid resorting to replacing an implant should a patient need a different refractive power lens may be found in U.S. patent application Ser. No. 832,335, *Variable Refractive Power, Expandable Intraocular Lenses,* filed Feb. 24, 1986 by Peyman, commonly owned with this application by Gholam A. Peyman, M.D.

It would be expedient to offer an intraocular lens where the refractive power is fixed at implantation while offering the benefit of changing the refractive power subsequently with little or no surgical invasion and in a nearly atraumatic manner.

It would be desirable to offer an intraocular lens for very young patients where the refractive power is fixed at implantation while offering the benefit of changing the refractive power in calculated degrees subsequently as the very young patients mature with little or no surgical invasion, in a nearly atraumatic manner and on an "outpatient" basis.

BRIEF DESCRIPTION OF THE INVENTION

The intraocular lens of this invention is designed for insertion into the posterior chamber or in the capsular bag of the eye of a mammal. Central lenticular means refracts light that will enter the eye through the cornea before the light passes to the retina. The central lenticular means preferably is made from a flexible, impermeable, physiologically compatible, solid material having a free standing shape retaining configuration throughout its solid form, for example silicone. The central lenticular means has at least one chamber means therein. Lenses having one chamber means therein utilize an exterior face of the central lenticular means as refractive, rupturable membrane means. Lenses having at least two chamber means therein can use the exterior faces of the central lenticular means as refractive, rupturable membrane means, can have the chamber means separated by relatively thin, refractive, rupturable membrane means which establishes a refractive surface and which contributes to the lens' refractive power or can use both the exterior faces of the central lenticular means as refractive, rupturable membrane means and have the chamber means separated by relatively thin, refractive, rupturable membrane means. The chamber means are either evacuated or filled with fluid or material that can have a refractive index different from the central lenticular means and the refractive, rupturable membrane means. Preferably, the fluid or material is a physiologically compatible substance such as silicones, gelatins, polyvinyl alcohols or the like.

The central lenticular means can be biconvex, convex-plain, or convex-concave. Haptic means, feet or loops are attached to the central lenticular portion and function to hold the lens in place in the eye. Haptic means commonly are made from polypropylene or other synthetic polymers. Generally, the lenses have at least two haptic means, but intraocular lenses with more than two haptic means are not uncommon. First ends of the haptic means are fixed to the central lenticular means.

As eye shape and size change when very young cataract patients mature, an intraocular lens' refractive power correctly chosen during surgery may become incorrect as the distance from the lens to the retina changes. Light no longer is focused on the retina and visual acuity suffers. Eye glasses or contact lenses have been employed to correct a patient's vision in such instances. Otherwise, patients must undergo additional, conventional surgery to remove and replace the implanted lenses.

With this invention, however, subsequent surgical procedures would be less invasive since replacement of the implanted lenses is not indicated. More significant, though, is that surgical intervention via incision can be eliminated altogether. Using a Yttrium-Aluminum Garnet (YAG) laser, an exterior face of the central lenticular means functioning as refractive, rupturable membrane means or the refractive rupturable membrane means separating chamber means can be ruptured, vaporized or both to permit changing of the refractive power of the lens while the solid central lenticular means substantially retains its free standing configuration. In lenses having at least two chamber means therein, a face of the central lenticular means functioning as refractive, rupturable membrane means and refractive, rupturable membrane means separating chamber means both can be ruptured or vaporized. The result is the elimination of refractive surfaces of the lens. Eliminating refractive surfaces in this manner changes the refractive power of the lens. The precise amount of change in refractive power will be known before implant.

Intraocular lenses with more than two chambers therein, each separated by relatively thin, refractive, rupturable membrane means would allow a series of lens refractive power changes to take place at chosen intervals. Initially, a YAG laser of relatively low power would be used to rupture the most anterior membrane. Later, if another change in the lens' refractive power is indicated, stronger powered laser pulses would be used to rupture the more posterior refractive, rupturable membrane means in the implanted lens thereby changing the lens' refractive power again.

A benefit provided by this invention is that the refractive power of an intraocular lens can be precisely chosen to correct eyesight at the time of implant while also offering the advantage of changing the refractive power subsequently with no or minimal invasion.

Another benefit of this invention is that an intraocular lens is provided for very young cataract patients to correct eyesight for immediate needs while offering the benefit of changing the refractive power to a calculated degree subsequently as the very young patients mature with little or no surgical invasion, in a nearly atraumatic manner and on an "out-patient" basis.

Other benefits and advantages of this invention will become apparent upon reading the following detailed description and appended claims.

BRIEF DESCRIPTION OF THE DRAWINGS

For a more complete understanding of this invention, reference should now be had to the embodiments illustrated in greater detail in the accompanying drawings.

In the Drawings.

DESCRIPTION OF THE PREFERRED EMBODIMENTS

Figure 1:
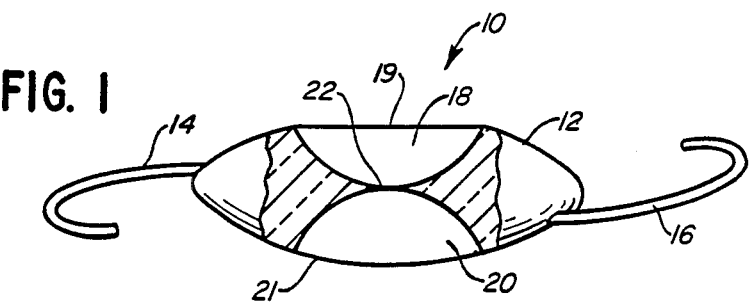
FIG. 1 is a perspective view of an embodiment of the intraocular lens of the present invention having two chamber means therein and showing a central lenticular means with a flat anterior surface.

One embodiment of the intraocular lens 10 of this invention is illustrated in FIG. 1. Intraocular lens 10 has central lenticular means 12 and haptic means 14 and 16. Preferably, central lenticular means 12 is made from a solid, flexible, impermeable, physiologically compatible material conventionally available. Resilient haptic means 14, 16 preferably are made from polypropylene, other polyolefin, polymethylmethacrylate, or the like. Resilient haptic means 14, 16 are fixedly attached to central lenticular means 12 and act to stabilize implanted intraocular lens 10.

Central lenticular means 12 of intraocular lens 10 has chamber means 18 and 20 therein. Chamber means 18, 20 are separated by single, refractive rupturable membrane means 22. Flat, exterior surface 19 positioned anteriorly on central lenticular means 12 can function as refractive, rupturable membrane means. Similarly, exterior surface 21 positioned posteriorly on central lenticular means 12 can function as refractive, rupturable membrane means. Chamber means 18, 20 preferably are filled with a physiologically compatible fluid such as silicones, gelatins, polyvinyl alcohol and gases. Alternatively chamber means 18, 20 can be evacuated.

Figure 2:
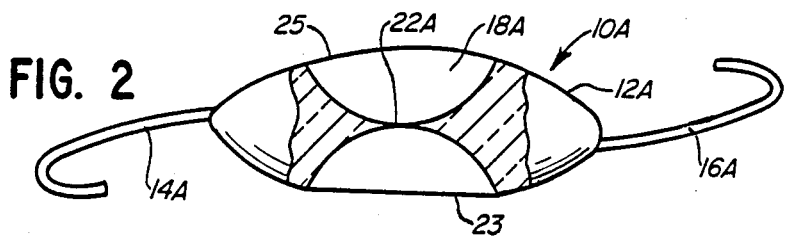
FIG. 2 is a perspective view of an embodiment of the intraocular lens of the present invention having two chamber means therein and showing a central lenticular means with a flat posterior surface.

Intraocular lens 10 shown in FIG. 1 has a flat, exterior surface 19 positioned anteriorly on central lenticular means 12. FIG. 2 illustrates intraocular lens 10A having flat, exterior surface 23 positioned posteriorly on central lenticular means 12A. Flat, exterior surface 23 positioned posteriorly on central lenticular means 12A can function as refractive, rupturable membrane means. Similarly, exterior surface 25 positioned anteriorly on central lenticular means 12A can function as refractive, rupturable membrane means. Resilient haptic means 14A, 16A are fixedly attached to central lenticular means 12A. Chamber means 18A, 20A are separated by single refractive, rupturable membrane means 22A.

Figure 3:
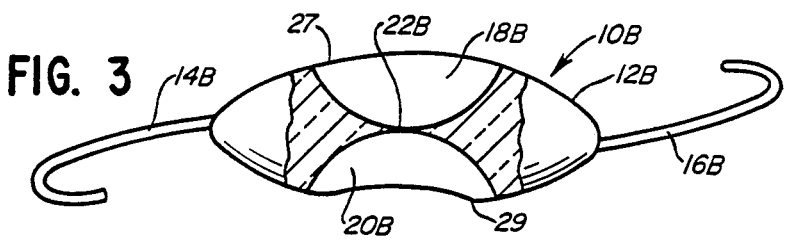
FIG. 3 is a perspective view of an embodiment of the intraocular lens of the present invention having two chamber means therein and showing a convex-concave central lenticular means.

FIG. 3 illustrates intraocular lens 10B having convex-concave central lenticular means 12B. Resilient haptic means 14B, 16B are fixedly attached to central lenticular means 12B. Chamber means 18B, 20B are separated by single, refractive rupturable membrane means 22B. Anterior and posterior external surfaces 27, 29 on central lenticular means 12B can function as refractive, rupturable membrane means.

Figure 4:
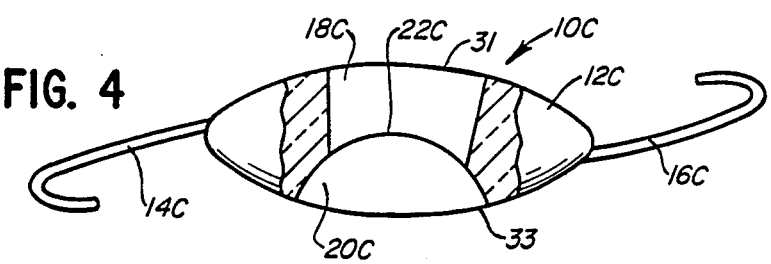
FIG. 4 is a perspective view of an embodiment of the intraocular lens of the present invention having two chamber means therein and showing a convex-convex central lenticular means.

Similarly, FIG. 4 illustrates intraocular lens 10C having convex-convex central lenticular means 12C. Resilient haptic means 14C, 16C are fixedly attached to central lenticular means 12C. Chamber means 18C, 20C are separated by a single, refractive rupturable membrane means 22C. Anterior and posterior external surfaces 31, 33 on central lenticular means 12C can function as refractive, rupturable membrane means.

Figure 7:
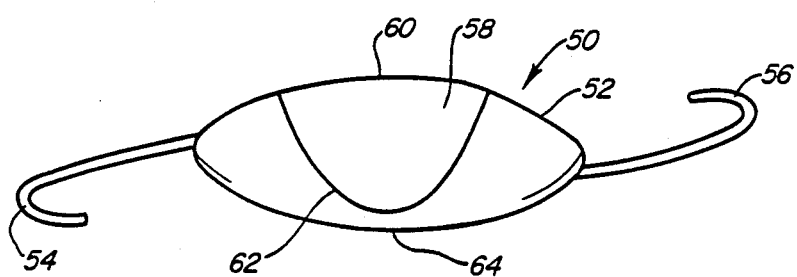
FIG. 7 is a perspective view of an embodiment of the intraocular lens of the present invention having one chamber means therein and showing a convex-convex central lenticular means.

FIG. 7 illustrates intraocular lens 50 in another embodiment of this invention. Intraocular lens 50 has central lenticular means 52 and haptic means 54 and 56. Preferably, central lenticular means 52 is made from a solid, flexible, impermeable, physiologically compatible material conventionally available. Resilient haptic means 54, 56 preferably are made from polypropylene, other polyolefin, polymethylmethacrylate, or the like. Resilient haptic means 54, 56 are fixedly attached to central lenticular means 52 and act to stabilize implanted intraocular lens 50 in the eye.

Central lenticular means 52 of intraocular lens 50 has chamber means 58. Chamber means 58 preferably is filled with a physiologically compatible fluid such as silicones, gelatins, polyvinyl alcohol and gases. Alternatively, chamber means 58 can be evacuated. Exterior surface 60 positioned anteriorly on central lenticular means 52 functions as refractive, rupturable membrane means. Refractive surface 62 has a curvature different from refractive surface 64. It should be appreciated that, depending on placement in the eye, exterior surface 60 can be positioned either anteriorly or posteriorly on central lenticular means 52.

Figure 5:
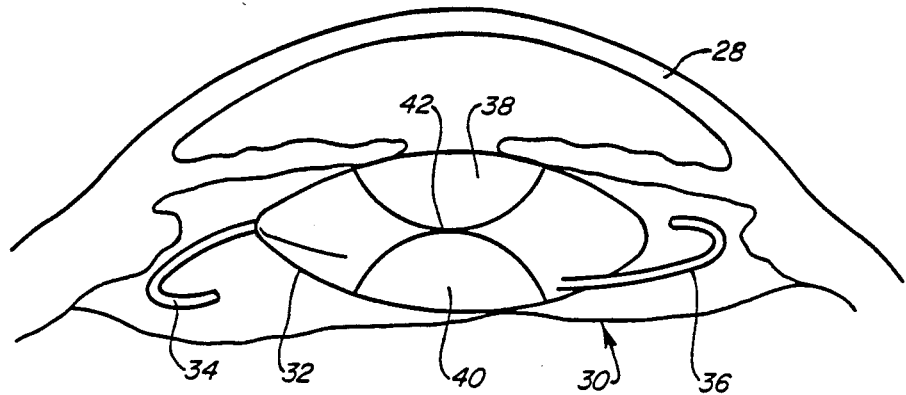
FIG. 5 is a cut-away view of a mammalian eye showing the intraocular lens of the present invention implanted in the eye and showing the refractive, rupturable membrane means intact.
Figure 6:
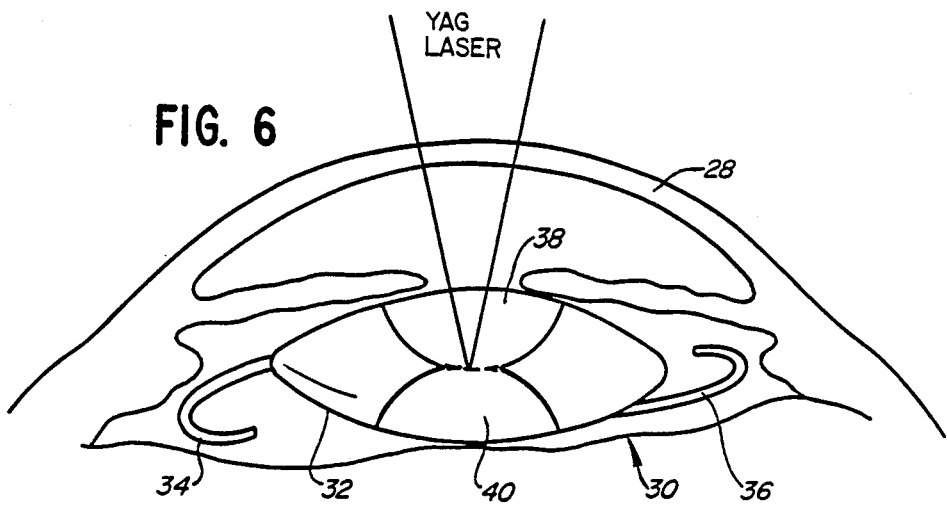
FIG. 6 is a cut-away view of a mammalian eye showing the intraocular lens of the present invention implanted in the eye and also showing a YAG laser disrupting the refractive, rupturable membrane means.

FIGS. 5 and 6 show intraocular lens 30 implanted in the eye of a mammal. FIG. 5 illustrates intraocular lens 30 implanted in eye 28. Resilient haptic means 34, 36 are fixedly attached to central lenticular means 32. Chamber means 38, 40 are separated by refractive, rupturable membrane means 42. Preferably, solid central lenticular means 32 is made from silicone, but any material conventionally used is suitable.

Significantly, FIG. 6 illustrates that the refractive power of intraocular lens 30 can be changed subsequent to implantation. This is accomplished without removing intraocular lens 30 and without surgical incision. Using a YAG laser, refractive, rupturable membrane means 42 separating chamber means 38, 40 is ruptured or vaporized. Refractive, rupturable membrane means 42 acting as a refractive surface disappears. Intraocular lens 30 would have a resulting refractive power determined by the remaining refractive surfaces of central lenticular means 32 and the fluid, if any, in the newly combined chamber means 38, 40.

Single refractive, rupturable membrane means shown in the embodiments of the intraocular lenses of this invention illustrated in the figures can be ruptured subsequent to implantation in the eye, thus changing the refractive power of the lens. Similarly, in lenses having at least two chamber means therein and more than one refractive, rupturable membrane means, one or more of the refractive, rupturable membrane means can be ruptured subsequent to implantation in the eye. Consequently, the refractive power of the lens can be changed to greater extent in a single procedure or in successive procedures in calculated degrees.

A singular benefit of this invention resides in that refractive power of the implanted lens can be changed subsequent to implantation, without removing the intraocular lens, and with minimal or no trauma. This benefit is particularly important to patients who are very young. Eye size change in very young patients as they mature thus necessitates a reduction in intraocular lens refractive power.

The above has been offered for illustrative purposes and is not intended to limit the invention of this application which is defined in the claims below.

I claim:

1. Intraocular lens for implantation inside the eye of a mammal comprising:
    solid central lenticular means having a free standing shape retaining configuration throughout its solid form for refracting light entering the eye through the cornea before light passes to the retina, said solid central lenticular means having at least one chamber means therein and having at least one refractive, rupturable membrane means whereby said refractive, rupturable membrane means are rupturable subsequent to eye implantation thus permitting changing the refractive power of said intraocular lens while said solid central lenticular means substantially retains its free standing configuration.

2. The intraocular lens of claim 1 wherein said chamber means is filled with a material having an index of refraction different from the index of refraction of said solid central lenticular means and said refractive, rupturable membrane means.

3. The intraocular lens of claim 1 wherein said chamber means is evacuated and has an index of refraction different from the index of refraction of said solid central lenticular means and said refractive, rupturable membrane means.

4. The intraocular lens of claim 1 additionally comprising at least two resilient haptic means for stabilizing and holding in place in the eye said central lenticular means.

5. The intraocular lens of claim 2 additionally comprising at least two resilient haptic means for stabilizing and holding in place in the eye said central lenticular means.

6. The intraocular lens of claim 3 additionally comprising at least two resilient haptic means for stabilizing and holding in place in the eye said central lenticular means.

7. The intraocular lens of claim 2 wherein said material filling said chamber means consists essentially of a material selected from the group consisting of physiologically compatible gases, silicones, gelatins and polyvinyl alcohols.

8. The intraocular lens of claim 5 wherein said material filling said chamber means consists essentially of a material selected from the group consisting of physiologically compatible gases, silicones, gelatins and polyvinyl alcohols.

9. Intraocular lens for implantation inside the eye of a mammal comprising:

solid central lenticular means for refracting light entering the eye through the cornea before light passes to the retina, said solid central lenticular means having at least two chamber means therein separated by refractive, rupturable membrane means, said chamber means filled with a material having an index of refraction different from the index of refraction of said solid central lenticular means and said refractive, rupturable membrane means whereby said refractive, rupturable membrane means are rupturable subsequent to eye implantation thus permitting changing the refractive power of said intraocular lens.

10. The intraocular lens of claim 9 additionally comprising at least two resilient haptic means for stabilizing and holding in place in the eye said central lenticular means.

11. The intraocular lens of claim 9 wherein said material filling said chamber means consists essentially of a material selected from the group consisting of physiologically compatible gases, silicones, gelatins and polyvinyl alcohols.

12. The intraocular lens of claim 10 wherein said material filling said chamber means consists essentially of a material selected from the group consisting of physiologically compatible gases, silicones, gelatins and polyvinyl alcohols.

13. Intraocular lens for insertion inside the eye of a mammal comprising:

solid central lenticular means for refracting light entering the eye through the cornea before light passes to the retina, said solid central lenticular means having at least two chamber means therein separated by refractive, rupturable membrane means, said chamber means being evacuated and having an index of refraction different from the index of refraction of said solid central lenticular means and said refractive, rupturable membrane means whereby said refractive, rupturable membrane means is rupturable subsequent to eye implantation thus permitting changing the refractive power of said intraocular lens.

14. The intraocular lens of claim 13 additionally comprising at least two resilient haptic means for stabilizing and holding in place in the eye said central lenticular means.

* * * * *